United States Patent
Agam et al.

(10) Patent No.: US 10,206,949 B2
(45) Date of Patent: Feb. 19, 2019

(54) COMPOSITION THAT RELIEVES HEARTBURN, GERD AND HANGOVERS

(71) Applicants: Ofer Agam, Daly City, CA (US); Francis Rhett Brockington, Columbia, SC (US)

(72) Inventors: Ofer Agam, Daly City, CA (US); Francis Rhett Brockington, Columbia, SC (US)

( * ) Notice: Subject to any disclaimer, the term of this patent is extended or adjusted under 35 U.S.C. 154(b) by 0 days.

(21) Appl. No.: 15/244,116

(22) Filed: Aug. 23, 2016

(65) Prior Publication Data
US 2017/0080023 A1 Mar. 23, 2017

Related U.S. Application Data

(60) Provisional application No. 62/221,147, filed on Sep. 21, 2015.

(51) Int. Cl.
| | |
|---|---|
| *A61K 33/10* | (2006.01) |
| *C07K 16/00* | (2006.01) |
| *C07K 16/28* | (2006.01) |
| *A61K 9/48* | (2006.01) |

(52) U.S. Cl.
CPC ............ *A61K 33/10* (2013.01); *A61K 9/4875* (2013.01); *C07K 16/00* (2013.01); *C07K 16/2887* (2013.01); *C07K 2317/14* (2013.01); *C07K 2317/41* (2013.01); *C07K 2317/524* (2013.01); *C07K 2317/70* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 4,327,076 | A | * 4/1982 | Puglia | A23G 3/36 424/441 |
| 4,533,543 | A | * 8/1985 | Morris | A61K 33/06 424/441 |
| 4,605,551 | A | * 8/1986 | Buehler | A61K 9/0056 424/498 |
| 9,315,503 | B2 | 4/2016 | Van Niel et al. | |
| 9,353,217 | B2 | 5/2016 | Tanahashi et al. | |
| 2016/0228446 | A1 | 8/2016 | Greshock et al. | |

OTHER PUBLICATIONS http://oilhealthbenefits.com/almond-oil/ referenced on Feb. 12, 2018.*
https://www.webmd.com/vitamins-supplements/ingredientmono-915-MEDIUM+CHAIN+TRIGLYCERIDES+MCTs.aspx referenced on Feb. 13, 2018.*
http://www.kerfootgroup.co.uk/oil-inventory/sweet-almond-oil-refined-usp29 referenced on Feb. 13, 2018.*
https://www.drugs.com/dosage/calcium-carbonate.html referenced on Feb. 13, 2018.*
Salager, J. L. Surfactants Types and Uses. FIRP Booklet #E300—A Teaching Aid in Surfactant Science and Engineering, pp. 1-50, 2002.*

* cited by examiner

*Primary Examiner* — Jessica Worsham
(74) *Attorney, Agent, or Firm* — F. Rhett Brockington

(57) ABSTRACT

A composition and an article of manufacture providing relief of indigestion, heartburn, GERD and some hangovers. The composition is an oleophilic colloidal suspension of a finely ground powder of USP calcium carbonate suspended in a usually tasteless edible oil; wherein the suspension has a weight ratio range of oil to calcium carbonate that is from about 1.0 (oil) to 0.25 (calcium carbonate) to about 1.0 (oil) to 2.2 (calcium carbonate); and a single dose has a calcium carbonate weight range from about 200 mg to about 1000 mg. The composition can include other foods and additives so that it may be used and dispensed in a plurality of delivery systems and foods. The oleophilic colloidal suspension can be dispensed as a soft-gel.

6 Claims, No Drawings

COMPOSITION THAT RELIEVES HEARTBURN, GERD AND HANGOVERS

CROSS-REFERENCE TO RELATED APPLICATION

The present patent application/patent claims the benefit of priority of U.S. Provisional Patent Application No. 62/221,147, filed on Sep. 21, 2015, and entitled "A COMPOSITION THAT RELIEVES HEARTBURN, GERD AND HANGOVERS", the contents of which are incorporated in full by reference herein.

FIELD OF THE INVENTION

The invention relates generally to healthful food based supplements, and in particular to compositions that mitigate heartburn, GERD, and hangovers.

BACKGROUND

More than a third of the population in the United States occasionally has heartburn, and about one-in-ten people have it daily. Infrequent heartburn does not usually have any serious consequences, but frequent heartburn (recurring more than twice per week) can result in severe side-effects. Early management is important to maintain one's health.

A working explanation of heartburn requires an understanding of the structure and action of the esophagus. The esophagus is a tube that connects one's throat to their stomach. The esophagus of an adult is about 10 in (25 cm) long, and it is lined with squamous (plate-like) epithelial cells, coated with mucus, and surrounded by muscles that push food to the stomach by sequential waves of contraction (peristalsis). The lower esophageal sphincter (LES) is a thick band of muscles that encircles the esophagus just above the uppermost part of the stomach. This sphincter is usually tightly closed and normally opens only when food passes from the esophagus into the stomach. Thus, the contents of the stomach are normally kept from moving back into the esophagus. An exception to this is when one burps, the LES opens potentially enabling acid reflux.

The stomach has a thick mucus coating that protects it from the strong acid that is secreted into the interior of the stomach when food is present. The much thinner esophageal coating doesn't provide protection against acid. Thus, if the LES opens inappropriately or fails to close completely, potentially some stomach contents could leak into the esophagus, where the acid can burn the esophagus. The resulting burning sensation is called heartburn.

Occasional heartburn has no serious long-lasting effects, but repeated episodes of gastroesophageal reflux can ultimately lead to esophageal inflammation (esophagitis) and other damage. If episodes occur more frequently than twice a week, and the esophagus is repeatedly subjected to acid and digestive enzymes from the stomach, ulcerations, scarring, and thickening of the esophagus walls can result. This thickening of the esophagus wall causes a narrowing of the interior of the esophagus. The narrowing affects swallowing and peristaltic movements. Repeated irritation can also result in changes in the types of cells that line the esophagus. The condition associated with these changes is termed Barrett's syndrome and can lead to esophageal cancer.

A number of different factors may contribute to LES malfunction with its consequent gastroesophageal acid reflux. They include: eating large meals that distend the stomach causing the LES to open. Lying down within two to three hours of eating can cause the LES to open. Obesity, pregnancy, and tight clothing can impair the ability of the LES to stay closed by putting pressure on the abdomen. Certain drugs, notably nicotine, alcohol, diazepam (Valium), meperidine (Demerol), theophylline, morphine, prostaglandins, calcium channel blockers, nitrate heart medications, anticholinergic and adrenergic drugs (drugs that limit nerve reactions), including dopamine, can relax the LES. Progesterone is thought to relax the LES. Even greasy foods and some other foods such as chocolate, coffee, and peppermint have been reported to relax the LES. Paralysis and systemic scleroderma can cause the LES to malfunction. Hiatus hernia may also cause heartburn according to some gastroenterologists. Hiatus hernia is a protrusion of part of the stomach through the diaphragm to a position next to the esophagus.

Heartburn itself is a symptom. Other symptoms also caused by gastroesophageal reflux can be associated with heartburn. Often heartburn sufferers can salivate excessively or can regurgitate (burp) stomach contents into their mouths, leaving a sour or bitter taste. Frequent gastroesophageal reflux leads to additional complications including difficult or painful swallowing, sore throat, hoarseness, coughing, laryngitis, wheezing, asthma, pneumonia, gingivitis, halitosis and earache.

The literature reports that occasional heartburn is commonly treated with over-the-counter antacids. These products go straight to the esophagus and immediately begin to decrease acidity. However, they should not be used as the sole treatment for heartburn sufferers who either have two or more episodes per week or who suffer for periods of more than three weeks. There is a risk of kidney damage and other metabolic changes.

H2 blockers are acid reducers for Gastroesophageal Reflux Disease (GERD). Chemically, they are histamine receptor blockers which inhibit the formation of stomach acid, and mechanistically they are relatively slow acting. Examples include famotidine in Pepsid AC™ which is a product of McNeil Consumer Pharmaceuticals Co., ranitidine in Zantac™ which is a product of Boehringer Ingelheim Pharmaceuticals, Inc, cimetidine in Tagamet™ which is a product of Prestige Brands, Inc, and nizatidine in Axid™ which was developed by Eli Lilly. The IUPAC name for famotidine is 3-([2-(diaminomethyleneamino)thiazol-4-yl] methylthio)-N'-sulfamoyl-propanimid-amide. The IUPAC name for cimetidine is 2-cyano-1-methyl-3-(2-[(5-methyl-1H-imidazol-4-yl)-methylthio]ethyl) guanidine. Famotidine is reputed to be 30 times more active than cimetidine. In Famotidine, the imidazole-ring of cimetidine is replaced with a 2-guanidinothiazole ring. Clinically, famotidine has been found to be 30 times more active than cimetidine. The IUPAC name for ranitidine is N-(2-[(5-[(dimethylamino) methyl]furan-2-yl) methylthio]ethyl)-N'-methyl-2-nitroethene-1,1-diamine. It should be noted that ranitidine is also known to give false positives for methamphetamine on drug tests. The IUPAC name for nizatidine is N-(2-[(2-[(dimethylamino)methyl]thiazol-4-yl)methylthio]ethyl)-N-methyl-2-nitroethene-1,1-diamine.

Ranitidine is reported to decrease mucosal perfusion in patients with acute renal or cardiac failure, and increases their risk of death. Fungal sepsis has been observed in some patients on ranitidine. All drugs in its class decrease gastric intrinsic factor secretion, which can significantly reduce absorption of protein-bound vitamin $B_{12}$ in humans. Elderly patients taking H2 receptor antagonists are more likely to require $B_{12}$ supplementation than those not taking such drugs. H2 blockers may also reduce the absorption of drugs (azole antifungals, calcium carbonate) that require an acidic stomach. By suppressing acid-mediated breakdown of proteins, antacid preparations such as ranitidine may lead to an elevated risk of developing food or drug allergies, due to undigested proteins, which can then pass into the gastrointestinal tract, wherein sensitization occurs. Whether this risk occurs with only long-term use or with short-term use, as well, is unclear. Ranitidine and other histamine H2 receptor antagonists may increase the risk of pneumonia in hospitalized patients. They may also increase the risk of community-acquired pneumonia in adults and children. Multiple studies suggest that the use of H2 receptor antagonists, such as ranitidine, may increase the risk of infectious diarrhea, including traveler's diarrhea and salmonellosis.

In general, H2 antagonists increase the risk of developing food allergies. Patients who take these agents develop higher levels of Immunoglobulin E (IgE). IgE is a class of antibody found in mammals that provides important immune defense. IgE also plays an essential role in type I hypersensitivity, which manifests various allergic diseases, such as allergic asthma, most types of sinusitis, allergic rhinitis, food allergy, and some types of chronic urticaria and atopic dermatitis. IgE also plays a pivotal role in allergic conditions, such as anaphylactic reactions to certain drugs, bee stings, and antigen preparations used in specific desensitization immunotherapy.

H2 blockers are usually effective at preventing heartburn, but not stopping an ongoing episode. H2 blocker treatment also allows healing of esophageal damage, but is not very effective when there is a high degree of damage. It takes 30-45 minutes for these drugs to take effect, so they must be taken prior to an episode. Thus, they should be taken daily, usually two to four times per day for several weeks. Six to 12 weeks of standard-dose treatment relieves symptoms in about one-half the patients. Higher doses relieve symptoms in a greater fraction of the population, but at least 25% of heartburn sufferers are not helped by H2 blockers.

LES is reportedly lessened with prokinetic agents (also known as motility drugs), stimulating it to close more tightly, thereby retaining the stomach contents out of the esophagus. Typically, prokinetic agents can also stimulate contractions of the colon, and an argument could be made that prokinetic agents are largely laxatives.

Proton Pump Inhibitors (PPIs) are the newest class of drugs to reduce heartburn, GERD and acid reflux. The stomach wall has cells that pump acid into the stomach. The reported mechanism is that the PPI binds irreversibly to a hydrogen/potassium ATPase enzyme (i.e. proton pump) on gastric parietal cells, which blocks the secretion of hydrogen ions; where the protons combine with chloride ions in the stomach lumen to form gastric acid. Proton Pump Inhibitors include: Aciphex™ (raberprazole) is a product of Eisai Inc, Nexium™ (esomeprazole) is a product of AstraZeneca, Prevacid™ (lansoprazole) is a product of Novartis, Prilosec™ (omeprazole) is a product of Proctor and Gamble, and Protonix™ (pantoprazole) is a product of Pfizer. With many PPI's very serious interactions can occur with alcohol, and the most common side effect includes headache, and diarrhea.

The latest concern is that long term use of PPIs is increased bone fractures, low vitamin B12, and low magnesium levels. Furthermore, PPIs might increase the risk for dementia. Britta Haenisch and colleagues at the German Center for Neurodegenerative Diseases in Bonn studied 73,679 people ages 75 and older. The researchers found regular PPI users had at least a 44 percent increased risk of dementia compared with those not using the drugs.

Antacids that mechanistically work by reacting with stomach gastric acid, which contains hydrochloric acid (HCL), can potentially produce a gas, for example carbon dioxide. It has been speculated that the gas causes foaming within the stomach, and the bubbles then convey gastric acid past the LES into the esophagus. The pH of the stomach gastric acid is 1.5 to 3.5 (around 0.5%, or 5000 parts per million). The acid plays a key role in digestion of proteins, by activating digestive enzymes, and making ingested proteins unravel so that digestive enzymes break down the long chains of amino acids. The hydrochloric acid is at a relatively low acid concentration, and the acid functions more catalytically than reactively. Reputedly, there are some cells in the stomach that produce bicarbonate, a base, to buffer the fluid, ensuring that it does not become too acidic, so the stomach is capable of handling carbonate and bicarbonate without heart burn.

SUMMARY OF THE INVENTION

The disclosed invention is an oleophilic colloidal suspension having a density that is higher than water and is immiscible with water and water based fluids like gastric acid. The oleophilic colloidal suspension includes a relatively high density powder suspended in an edible oil, and typically, the oleophilic colloidal suspension at body temperature is a fluid. A preferred high density powder is a metal salt of a weak acid. Exemplary of the metal salt compound is calcium carbonate. Calcium carbonate has a density that is about 2.7 g ml, and is also an antacid. Calcium, which is necessary for bones, is often depleted by H2 blockers and PPI's, suggesting that if H2 blockers and PPI's are prescribed, then the disclosed invention can be taken to mitigate bone loss.

This combination of properties, which include fluidity, high density, immiscible with water, enables the oleophilic colloidal suspension to flow when ingested, coating the squamous (plate-like) mucous lined epithelial cells of the esophagus and the lining cells of the stomach. The oleophilic colloidal suspension (referred to as OCS in this document) is substantially immiscible with gastric acid, and most of the watery contents of the stomach, so that in the presence of water or gastric acid the OCS is repelled, causing the OCS to be distributed onto the stomach wall, therein coating the walls.

An aspect of the invention is that at body temperature, when taken orally, OCS coats the esophagus, and flows onto the stomach walls, coating the lining walls of stomach. The contents of the stomach are substantially hydrophilic, therefore the OCS has better wetting of the cellular wall that makes up the interior lining of the stomach. A parallel comparison can be found in the ease that human skin is wetted by oil versus water. A surfactant is required for water to wet human skin, as the skin typically has a thin protective coating of oil.

Mechanistically, coating is augmented by the higher density of the OCS and the immiscibility with the gastric juices. The lower density gastric juices and other stomach contents are in interfacial contact with the OCS, wherein the gastric juices and other stomach contents are pressing downward, forcing a portion of the OCS to flow outward, wherein OCS forms a coating on the stomach walls. The OCS coating provides a barrier layer between the walls of the stomach and the contents of the stomach. The suspended antacid in the OCS is coated with the edible oil. The more oil, the greater the depth of the coating of the edible oil.

A distinction of the invention from the prior art is that the antacid has a density that is greater than water. The total composition of the OCS enables that antacids having a density less than water can be included in the OCS, so long as the OCS has enough high density colloidal powder suspended in the edible oil to raise the density of the total composition of the OCS to where it is greater than water. The loading level of the high density powder is high enough to compensate for the relatively low density of most edible oils. Most edible oils have a density of about 0.9 g/ml, while water has a density of about 1 g/ml. Typically, H2s and PPIs are compressed powders, and their density is ~1 g/m or lower, and wouldn't have a high enough density to increase the density of the edible oil. In the powder form, even high density metal salt powders, such as calcium carbonate, have a bulk density of about 0.72 g/ml, and a tamped density of about 1.2 g/ml. The actual density of calcium carbonate is ~2.7 g/ml, almost 3× the density of most edible oils.

Another aspect of the invention is that the OCS is formulated using a high density finely ground powder that can be wetted by the edible oil, so that the high density metal salt powder approaches its actual density. In the case of calcium carbonate recall that the actual density is about 2.7 g/ml. So to raise the density of the OCS to about 1 g/ml, for every 1 gram of edible oil, only about 0.158 g of calcium carbonate will increase the density of the OCS to 1 g/ml. Doubling the weight of calcium carbonate increase the density to 1.08 g/ml. If other materials are added having a density less than water, additional high density powder that can be wetted by the edible oil must be added to raise the density of the OCS to where it is higher than water. Therein, the OCS can be formulated to have a density which is higher than water. Even when the OCS has a plurality of components that have a density that is lower than water, the density of the OCS can be raised by adding more calcium carbonate.

The invention provides relief from heartburn and most forms of GERD. Trials have also confirmed that OCS provides relief for alcohol hangovers and THC (marijuana) hangovers. There is a reduced craving for food and the often accompanying heartburn. Oils that have a high percentage of an omega-9 fatty acid, i.e. oleic acid, are the most effective. Omega-9 fatty acids reputedly satiate the craving for food, and the possible associated heartburn due to reflux.

An object of the invention is to utilize a sufficient fineness of grind powder such that there is no grittiness. Micron sized material has a very high surface area, and, unless the surface is protected by an edible oil, the antacid will react rapidly with the gastric acid. Ultimately, as the oil is absorbed or digested the antacid does come into contact with the gastric acid. In the intermediate time, the OCS soothes the cells and the lower esophageal sphincter (LES), and reflux is reduced as newly formed gastric acid is secreted by the parietal cells. Certain edible oils, known as Medium Chain Triglycerides oils (MCTs) can be absorbed in the stomach, and into the blood stream. MTCs are triglycerides whose fatty acids have an aliphatic tail of 6-12 carbon atoms. MCTs are triglycerides whose fatty acids have an aliphatic tail of 6-12 carbon atoms. The fatty acids found in MCTs are called medium-chain fatty acids (MCFAs). Like all triglycerides, MCTs are composed of a glycerol backbone and three fatty acids. In the case of MCTs, 2 or 3 of the fatty acid chains attached to glycerol are of medium length. Rich sources for commercial extraction of beneficial MCTs include palm kernel oil and coconut oil. Caproic acid has six carbon atoms. Caprylic acid has eight carbon atoms. Capric acid has ten carbon atoms, and Lauric acid has twelve carbon atoms. All MTCs are saturated. OCS that is formulated with MCFAs should be especially suitable for babies that have reflux.

Most heartburn medicines tend to stop or slow the digestion of the contents within the whole stomach as they are either dispersed in a watery medium and/or chunks suspended in salvia. The invented OCS concentrates its action on the stomach wall, and is therefore more effective because the active ingredients are not distributed throughout the volume of the stomach.

In one embodiment the OCS is substantially a creamy paste of an oil that has a moderate rate of absorption on skin. Examples of oils that fall into this category are jojoba, kuikuinut, argan, almond, coconut, and sunflower. An example of a slow absorbing oil is avocado oil, and an example of a fast absorbing oil is hazelnut. Olive oil has a medium rate of absorption, but because it has relatively low viscosity, it is usually combined with one or more other oils that are slower absorbing oils. In another embodiment the edible oil is high in omega-3 fatty acids, such as found in fish oil. Omega-3 fatty acid oils reputedly impart many healthful benefits.

One of the most effective oils is an extract of sweet almonds. Almonds are a seed that is drupe (which is not a true nut), where a drupe consists of an outer hull and a hard shell with the seed inside. A peach pit is another example of a drupe. Sweet almonds from the *Prunus amygdalus* fruit tree can be eaten raw, however the extracted almond oil is pasteurized, per California law, either by roasting or by steam distillation and oxygenated to neutralize flavonoids. The shelf life of almond oil using the latter process is typically about four years. Almonds from the fruit tree *Prunus dulcis* var. *amara* are bitter, and not edible as they contain substantial levels of hydrogen cyanide, which is a well-known poison. Currently, the FDA considers sweet almond oil as an essential oil that is edible, where the essential oil is an extract of a tree nut. It is considered GRAS under Title 21: PART 182, Subpart A—§ 182.20. Calcium carbonate is considered GRAS under Title 21: Part 184 Subpart B-Sec. 184.1191 of the FDA.

Other oils, such as animal oils can be effective, but because they typically have higher levels of saturated fats, they are less desirable, but in small portions can also be used, as previously discussed short chain acid triglycerides have unique applications with babies.

The OCS can furthermore include other components, such as other antacids, vitamins, antioxidants, surfactants, chelating agents, and viscosity modifiers.

As previously discussed, ingestion of the OCS mitigates heartburn. Heartburn is a symptom caused by a backflow of the stomach's acidic contents into the esophagus, causing inflammation and a sense of pain that can rise to the throat. The invention provides a methodology for compounding the OCS into a supplement having a composition that is gluten free. The supplement can be formed into an oral dose—for example a pill, a tablet, an enteric caplet, a soft-gel, a filled capsule; formed into a chewable supplement; formed into a candy such as a bar, a nugget; or into a liquid or powdered mixture that can be added to various foods to mitigate heartburn.

An aspect of the invention is that the edible oil in the OCS can include almond oil, and that the oil can be present as an oil, and also present as a component of whole or slivers or coarse pieces of almond; or included as a component of a ground material, for example an almond flour or an almond meal. The almonds can be skinless, blanched or roasted. Almonds are substantially gluten free, and therefore substantially devoid of gluten proteins. Gluten proteins can be divided into two main fractions according to their solubility in aqueous alcohols: the soluble gliadins and the insoluble glutens. Gluten proteins are found in wheat, and play a key role in water absorption capacity, cohesiveness, viscosity and elasticity on dough.

The amount of almond oil in an almond is generally from about 36% to about 60% of the weight of an almond. On average, the weight is about 44% oils. Of this weight percentage, about 62% is monounsaturated oleic acid (an omega-9 fatty acid), about 29% is linoleic acid (a polyunsaturated omega-6 essential fatty acid), and about 9% is saturated fatty acid.

Another aspect of the invention is that the OCS includes an antacid that is a metal salt of a relatively weak acid. Examples of a metal salt of a relatively weak acid, in addition to calcium carbonate which has been previously discussed, include magnesium carbonate, sodium carbonate and sodium bicarbonate. The metal is selected from those metals that form salts that are easily tolerated by a mammal's body, as exemplified by magnesium, calcium and sodium.

Another aspect of the invention is that the OCS can include an emulsifier to facilitate the suspension of the oil in water. Emulsified OCS has applications mostly as an additive to food.

Another aspect of the invention is that the OCS can include a flavoring additive. Non-limiting examples of the flavoring additive include almond extract, peppermint, spearmint, vanillin, bacon, chocolate, fruits, spices, honey, liquors (e.g., amaretto, schnapps, bourbons, and whiskeys), sweeteners and sugars. Almond extract has the benefit that not only is the flavor enhanced, but essential oils of almond have been found to enhance the effectiveness of the composition.

Evaporated milk, coffee creamers like Nestle Coffee-Mate™, milk flavors like Nestle Nesquik™, thickeners including maltodextrin, acacia, emulsifiers including lecithin, and carrageenan which is a family of linear sulfated polysaccharides that are extracted from red edible seaweeds that provide gelling, thickening, and stabilizing properties.

The OCS can be formulated to include preservatives to extend the shelf life of edible products. Sugar and table salt function as preservatives in that they are desiccants which draw-out water, therein causing bacteria to dehydrate. Other preservatives can include those that "Generally Recognized As Safe" (GRAS) those listed in the FDA, see Title 21, chapter 1, subchapter B, Part 182, Subpart D—Chemical Preservatives.

Also liquid smoke, which broadly is a product of burned wood chips can be added. Sodium meta-bisulfite and sodium sulfite are known to preserve food by preventing the growth of spoilage and pathogenic bacteria, and can be added, particularly in applications where meat may be present. Sodium lactate or potassium lactate can be used to extend shelf life.

An aspect of the invention is that the edible oil used to prepare the OCS is substantially free of water, and in trinsically has good stability.

The OCS can be formulated to include dry powder binders (excipients) such as microcrystalline-cellulose, methylcellulose, hydroxy methylcellulose, hydroxy-ethylcellulose, hydroxy-propylcellulose, and gelatins, which hold together dry powders compressed into a tablet or pill. Powdered egg whites can be included as a binder, as they are particularly effective for proteinaceous foods.

The composition of the OCS can include dark or light corn syrup. Dark corn syrup is a combination of corn syrup and molasses, caramel color and flavor, salt, and the preservative sodium benzoate. Dark corn syrup is a warm brown color and tastes richer than light corn syrup. The addition of corn syrup reduces crystallization of sugar.

As previously noted the composition of the OCS can include powdered milk, however, the addition of milk introduces lactose, which can be problematic for some. Sometimes tree nut oils such as Brazil nuts, cashews, chestnuts, filberts/hazelnuts, macadamia nuts, pecans, pistachios, and walnuts can be present in small quantities as a consequence of processing. Tree nuts and peanuts, unlike fruit nuts, have an increased risk of an allergic reaction.

Seeds such as safflower and sunflower seeds can be added, as they are a source of linoleic acid (an essential fatty acid), an excellent source of dietary fiber, some amino acids (especially tryptophan), vitamin E, Vitamin D, several B vitamins (especially thiamine, pantothenic acid, and folic acid). Additionally, they are rich in cholesterol-lowering phytosterols. Furthermore, sunflower seeds boast a low glycemic index as well as high levels of protein and minerals including magnesium and copper. As previously noted, almond oil has a high percentage of an omega-9 fatty acid.

The composition of the OCS can include low acidity oils, for example extra virgin oil, which 0.8% free acidity, and other oils such as coconut oils. The reader is directed to see a list of edible oils.

DETAILED DESCRIPTION OF THE INVENTION

The OCS is formulated to be effective in multiple forms. These forms include at least six product groups, where each product group imparts relief from heartburn and relief from GERD. A first product group includes compounding the OCS to include ingredients that impart a crunchy texture.

A second product group includes compounding the OCS into food, such as candy bars, ice creams, chili, snacks, or breads, which mitigate heartburn and reflux, thus enabling individuals to consume foods that otherwise wouldn't eat.

A third product group is encapsulating the OCS in a capsule, where an optimum capsule is a soft-gel. The soft-gel can be swallowed whole, or, alternatively, cracked open in a user's mouth therein releasing the OCS. Even when cracked open in the user's mouth the OCS is not gritty, and as it is swallowed it coats the user's throat and the walls of the stomach.

In a fourth product group, the OCS is typically more fluid, having a viscosity at room temperature from about one thousand centipoise to about ten thousand centipoise. The weight ratio range is from about 1.0 (oil):0.16 (calcium carbonate) to about 1.0 (oil):1.4 (calcium carbonate). Typically, the lower viscosity OCS is taken orally as a poured/measured liquid dose, or as a swig, or a squeezed amount. The OCS can be flavored, and as previously described contain colorants, preservatives, and other compatible antacids. The fourth product group is particularly suited for individuals who have strictures that prevent them from swallowing.

A fifth product group is a flavored chewable that includes the OCS.

A sixth product group is an OCS powder which includes an oil absorbing component such as maltodextrin, acacia, natural gums, starches, pectins, agar-agar and gelatin; wherein the OCS is converted to a granular powder, and the granular powder of OCS can be added to a beverage such as coffee and tea.

The invention provides relief from heartburn and most forms of GERD. Trials have also confirmed that it also provides some relief from the short term excess ingestion of one or more alcoholic beverages, such that following the short term excess ingestion there is indigestion, and other symptoms commonly referred to as hangover. Similarly, short term intake of marijuana can bring on a craving for food and accompanying heartburn, and the invention can reduce craving and reflux. The edible oil(s) in the OCS are typically selected to have a high percentage of an omega-9 fatty acid, such as oleic acid which is found in almond oil. Omega-9 fatty acids, which are naturally generated by the body in response to hunger, are readily available in the OCS to satiate the hunger. Alternatively, omega-3 fatty acids are not produced in the body, have been touted as being an appetite suppressant, and may also provide relief albeit by a different mechanism. Omega-3 fatty acids are found in fish oils. Taken together a combination of omega-9 and omega-3 would satiate the hunger and suppress the level of hunger.

The product groups have a common composition for a single dose, where the dose range is from about 200 mg to about 2500 mg of calcium carbonate, and a weight ratio range of oil to metal salt, where when the metal salt is calcium carbonate, the weight ratio range is from about 1.0 (oil):0.16 (calcium carbonate) to about 1.0 (oil):2.5 (calcium carbonate). The density of the OCS is always greater than water. The upper density of the OCS is about 1.73 g/ml. The lower limitation of calcium carbonate admixed with an oil (having a density of 0.91 g/ml) is about 0.16 grams of calcium carbonate per gram of oil. The upper limitation of calcium carbonate is viscosity limited and limited by the fineness of grind. When the median fineness of grind of calcium carbonate is greater than about 4 microns it is perceived as gritty, making it less palatable. At 4 microns, one 1 gram of warm almond oil can wet up to about 2.5 grams of calcium carbonate. The resulting OCS is a very thick stable paste, even when heated, and is about the upper limit for processing, especially into a soft-gel (see Third Product).

In general, the OCS has a much high density than water and it is at least as viscous as honey, and capable of flowing therein forming a coating layer as it spreads. Taken orally the viscous flow causes it to coat the squamous (plate-like) mucous lined epithelial cells of the esophagus and the cells lining the stomach wall. The viscous OCS is substantially immiscible with gastric acid, but it can wet the stomach wall, displacing gastric juices. Ingested as a liquid the OCS is largely confined to the interior surface of the esophagus and flows onto the interior wall of the stomach. In large part the OCS is much more attracted to the cellular wall of the stomach than any of the watery interior contents retained in an interior volume defined by the stomach.

The median fineness of grind of 4 microns is a good balance between size and cost. A median grind of 4 microns has some particles that are smaller and some that are larger. The finer the grind the higher the surface area to weight. In general, the higher the surface area the faster the potential rate is for neutralizing existing and freshly formed gastric acid, but this generalization is offset because with the higher surface area, viscosity builds faster, and more edible oil is required to achieve the same viscosity, and the extra oil typically slows the rate of neutralization. Neutralization and the oil soothes the cells and the lower esophageal sphincter (LES). Reflux is reduced. The oil itself is a small enough molecule that on skin it is up-taken by epithelial cells, and as previously discussed MCFAs can be absorbed through the stomach directly into the blood.

The gastric acid acts catalytically in concert with enzymes to break down the oil, which is a triglyceride of fatty acids. The enzymatic reaction reduces the triglycerides of the edible oils into fatty acids. The antacid neutralizes the gastric acid, which is nominally the source of GERD and heartburn.

The Tolerable Upper Intake Levels (UILs) for calcium is about 2-2.5 grams, although there are reports of people eating about 13 grams a day without experiencing hypercalcemia. Hypercalcemia is typically not caused by calcium carbonate, but from ingesting other forms of calcium, (calcium citrate), which reputed are more easily absorbed. Using the UIL for calcium of 2.5 grams, one would have to ingest at least 6.25 grams (or 6,250 mg) of calcium carbonate to approach 2.5 grams of calcium. The disclosed recommended upper dosage level of 1000 mg of calcium carbonate (1 gram) is less than 16% of the UIL.

The OCS is nominally made by incremental adding portions of calcium carbonate powder to the at least one edible oil, while it is being stirred. It has been found that an optimum weight ratio of oil:calcium carbonate ton is between 1:1.1 to 1:2.14, therein optimizing the amount of calcium carbonate in oil, where preferred oils include refined almond oil, canola oil and extra virgin olive oil. Fish oil and MCFA are also preferred oils, but Fish and MCFA oils do not have the thermal stability of refined almond oil, canola oil and extra virgin olive oil.

The ratio of oil to calcium carbonate is optimized for the intended application of the OCS. For example, if it is going into a soft-gel it must be thin enough to be processed on a soft-gel machine, yet viscous enough to provide a viscous coating with a relatively high density. Finely ground USP calcium carbonate is much less expensive that edible oils, and in particular refined almond oil. Almond oil cost ~16 times as much as USP calcium carbonate.

Digressing for a moment from the optimization for the intended application of the OCS, the Applicants remind the reader that calcium carbonate can neutralize gastric acid, and historically tablets of powdered calcium carbonate have been used as an antacid to neutralize the gastric juices present in the stomach. Taken as a chewed tablet or gummy, the swallowed chunks of the tablet admixe with the contents of the stomach, where if enough calcium carbonate is taken, eventually the entire stomach is neutralized and the parietal cells secreting the gastric acid in the stomach wall will be soothed relieving heartburn. Relatively large quantities of calcium carbonate are required as neutralization of the entire stomach contents is required. A downside of the neutralization of the entire stomach contents is that the reaction will produce bubbles which cause GERD. This is in contrast to the invention where neutralization is substantially limited to the esophagus and the lining of the stomach wall. Also, because calcium carbonate is only slightly soluble in water, a substantial percentage of the chunks will not be broken down, and will pass into the small intestine.

Returning to the OCS composition for soft-gels, the optimum ratio of almond oil to calcium carbonate is one near the limits of extruding the OCS. For almond oil and calcium carbonate having a finely ground powder of 4 microns (median) this spans the weight range ratio of about 1 g (oil):2.14 g (CC) to about 1 g (oil):1.4 g (CC). The higher ratio 1:2.14 is near the upper limits of loading of a calcium carbonate that is not gritty. If a coarser grind is used then a higher loading of calcium carbonate is possible, but grittiness increases. Almond oil is a carrier oil, and it is thicker than olive oil, but olive oil doesn't have as high of a percentage of the desired omega-9, albeit a higher loading of calcium carbonate could be possible because it is thinner. Refined almond oil has relatively good thermal stability, and processing at temperatures of about 180 F (about 82 C) is possible. The higher the temperature, the thinner the oil.

Using the ratio of about 1 g (oil):2.14 g (CC), an example of a soft-gel holding 450 mg of calcium carbonate, would include 210 mg of oil. To make about 1,000,000 soft-gels, to a heated mixer add ~210 Kg (231 L) of refined almond oil add ~450 Kg (~990 lbs, ~20 bags) of USP calcium carbonate in increments. Stir slowly and heat to about ~82 C until all the calcium carbonate is wetted. Using a high sheering mixing head stir rapidly sheer thins the mixture, and breaks up any lumps. The batch will make about 400 L (i.e. 106 gal) of a viscous OCS. Close the lid and pull a partial vacuum for several hours with slow stirring. Filter into a rotating pair of 25 gallon line pots. On the soft-gel machine, encapsulate the viscous OCS as round drops weighing ~660 mg in opposing pairs soft-gel half-molds for a No 12 oval soft-gel. Dry the soft-gels.

In the sixth product group a viscous OCS is converted into an OCS powder. Like the previous example the viscous OCS is a non-gritty antacid USP paste having a relatively high loading of calcium carbonate. The loading level is slightly lower because the viscosity has to be thin enough that a powder forming agent like maltodextrin or corn starch or acacia or a combination thereof can be dispersed throughout before the paste becomes a solid. Alternatively, the calcium carbonate can be added as a granular material already coated with an oil absorbing material, for example tapioca maltodextrin. If the OCS powder is ultimately going to be added to a liquid like coffee or tea or milk, then an emulsifier, for example lecithin will be needed. In one example, the optimum almond oil to calcium carbonate weight ratio is 1:1.7. Before or with the addition the calcium carbonate, about 0.05 weight of an emulsifier (i.e. lecithin) is added. Preservatives and flavoring agents should also be added before or with the addition the calcium carbonate. The resulting paste is similar in viscosity to toothpaste. To a stand mixer fitted with a relatively large vessel having a cover and equipped with a tined mixing head, add the paste with the emulsifier (and if used preservatives and flavoring agents). For every one gram of oil add 0.40 grams of maltodextrin (or a similar powdering agent). The paste turns into a granular powder in a matter of minutes, as the oily calcium carbonate is absorbed. The addition of another 0.23 grams for every one gram of oil and mixing with intermeshing blades converts the granular powder into a loose relatively fine powder. The volume is increased dramatically, but in water density is still higher than water. For 100 grams of the powder it has about 29 grams of almond oil, about 18 grams of Tapioca maltodextrin, about 49 grams of calcium carbonate, and about 5 grams of lecithin. One gram of the powder has 490 mg of calcium carbonate, which is within the target range of 200 mg to about 1000 mg of calcium carbonate for a single dose.

The powder can be tamped into a capsule. An "O" capsule has an interior volume of about 0.68 ml, and a "00" capsule has a volume of about 0.910 ml, so one "00" capsule can hold an adult dose. Medicinal powders can be incorporated. For example ibuprofen (Advil™), acetaminophen (Tylenol™) and acetylsalicylic (aspirin).

Alternatively, the powder can be delivered as a dry admixture with a creamer, like Nestle Coffee-mate or a generic creamer. The admixture can be packaged in individual packs or bulk packed, for example in a 6 to 32 oz. container. The container typically has a closeable spout.

Alternatively, the powder can be delivered as a dry admixture with a chocolate creamer, like Nestle Nesquik™ or a generic chocolate creamer. The admixture can be packaged in individual packs or bulk packed, for example in a 6 to 32 oz. container. The container typically has a removable top so that teaspoons and tablespoons quantities can be spooned out.

In another variation, the powder can be combined with a binder, such as such as microcrystalline-cellulose, methylcellulose, hydroxy-methylcellulose, hydroxy-ethylcellulose, hydroxy-propylcellulose, and gelatins, and compressed into a tablet or pill. Additionally tablets and pills can have acetylated mono-glycerides, anhydrous lactose, colloidal silicon dioxide, croscarmellose sodium, D&C yellow 10 aluminum lake, hypromellose, hypromellose phthalate, iron oxide yellow (iron oxide ochre), microcrystalline cellulose, mineral oil, polyethylene glycol (PEG)-400, polysorbate 80 and titanium dioxide. It may also contain: FD&C Yellow 6 aluminum lake, methacrylic acid copolymer, propylene glycol, starch, stearic acid, talc, and triacetin. Medicinal powders including ibuprofen, acetaminophen and aspirin can be incorporated.

The fourth product group is taken orally as a poured-measured liquid dose of the OCS, where OCS is fluid. The OCS has a non-gritty USP antacid, preferably calcium carbonate, suspended in at least one edible oil. In the embodiment the at least one edible oil is predominately refined almond oil. The almond oil to calcium carbonate ratio nominal range is from about 1:0.25 to about 1:4. The higher ratio is generally preferred as the content of the antacid is higher and the price is lower, and the higher the content of calcium carbonate the more bland the taste. An exception would be for very young children, and the oil would preferably be a MCFA, as MCFAs can be absorbed through the stomach directly into the blood. Another example would be where the at least one edible oil is fish oil.

The OCS can be flavored, for example with the addition of cacao (Bakers™ Baking Chocolate Bar, Unsweetened, 100% Cacao), Bakers™ Chocolate Baking Bar, Sweet, German's, 48% Cacao, Bakers™ Baking Chocolate Bar, Semi-Sweet, 56% Cacao or generic equivalents. An artificial sweetener, such as Splenda™, can be added as desired. Other flavoring additives including almond extract, peppermint, spearmint, vanillin, bacon, fruits, spices, honey, liquors (amaretto, schnapps, bourbons, whiskeys), sweeteners and sugars can be added.

The fifth product group, which is a flavored gummy, can be made in several ways. If a chocolate flavor is desired then a viscous OCS having a ratio of at least 1 (oil) to 1.7 (calcium carbonate) can be added directly to a chocolate recipe. For example a chocolate recipe typically has dark chocolate 45%-59% cacao, sugar, cocoa butter lecithin and vanilla, and melts at ~38 C (~96 (just below body temperature)). The addition of almond oil will depress the melting because cacao is soluble in almond oil. Sugar is substantially insoluble in almond oil. The amount of OCS that can be substituted is about 10%, before it starts affecting the melting point, provided that the OCS has a composition ratio of 1 (Oil) to 1.7 (calcium carbonate. If a portion of the almond oil is substituted with cacao, then more OCS can be added can be added without depressing the melting point. One ounce of chocolate having 10% OCS with a 1:1.7 ratio has 1.8 grams of calcium carbonate. A smaller bar, for example one that weighs 0.33 ounces, will have about 0.6 grams (600 mg) of calcium carbonate, which is within the desired dosage range. The actual cost of the chocolate bar could be further reduced with an increased loading of the calcium carbonate, and the bar would have fewer calories by increasing the weight of non-gritty calcium carbonate.

If another flavor (not chocolate) of the fifth product group chewable is desired this can be achieved using the powdered OCS with less maltodextrin and a gelatin formulation having the desired flavor and color. In one variation citric acid, food colorants, sugar and gelatin are dissolved in hot water, and then added to a mold having a release, and then cooled. After the gelatin in the molds has set up, a dollop of the powdered OCS is added, and then covered with additional gelatin formulation, and then cooled. In another variation, the OCS is emulsified in water, and the emulsion is used in place of pure water with the gelatin, citric acid, food colorants and sugar.

An example of the first product group, wherein the first product group is crunchy, is made using the third product group. The third product group can be made crunchy by adding coarsely ground nuts, almonds, pop-corn, grains, millet, seeds, quinoa, dried brown rice, buckwheat, oats, and cereals. Health bars high in fiber will then have enhanced calcium and a healthy source of omega-9.

The second product group has a relatively soft texture, and it is a less crunchy version of the first product group and/or a chewier version of the fifth product group that employs a gelatinous material. It includes candy formulations such as taffy, chewing gum, ice crème and breads (particularly cornbread), wherein the OCS incorporated into the recipe adding a healthful suspension of an antacid in oil. Many recipes call for an oil, and the inclusion of an omega-9 fatty acid would be healthful as well as mitigate heartburn and reflux that often accompanies the food.

The invention provides relief from alcohol hangovers and marijuana hangovers. There is a reduced craving for food and accompanying heartburn.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A fluid composition, said fluid composition consisting of:
   an oleophilic colloidal suspension (OCS) of a finely ground powder of calcium carbonate suspended in an almond oil, wherein both the calcium carbonate and the almond oil are Generally Recognized As Safe;
   said OCS has a density that is greater than 1 g/ml and less than 1.73 g/ml, is a fluid at body temperature, is immiscible with water and water based fluids including gastric acid, wherein the calcium carbonate in the OCS is insoluble in water, and the OCS is oleophilic with better wetting of a cellular wall that makes up an interior lining of a stomach;
   said OCS has a weight ratio range from about 1.0 (almond oil):0.16 (calcium carbonate) to about 1.0 (almond oil):2.14 (calcium carbonate);
   wherein, when ingested as a liquid, the combination of fluidity, higher density, and immiscibility with water causes said OCS, confined to interior surfaces of the esophagus, to flow onto interior walls of a stomach as the OCS is immiscible with watery interior contents retained within the stomach; and
   said OCS is largely devoid of taste.

2. The fluid composition according to claim 1, wherein said almond oil is a refined almond oil.

3. The fluid composition according to claim 1, wherein said calcium carbonate is not gritty, and has a median particle size of less than or equal to about 4 microns.

4. The fluid composition according to claim 1, wherein said OCS is encapsulated in a soft-gel.

5. The fluid composition according to claim 1, wherein the calcium carbonate has a median particle size of about 2.5 microns to about 4 microns.

6. The fluid composition according to claim 1, wherein the OCS is encapsulated in a pill.

* * * * *